United States Patent
Ueda

(10) Patent No.: US 12,096,912 B2
(45) Date of Patent: Sep. 24, 2024

(54) ENDOSCOPE TUBE WITH REINFORCING MEMBER WOUND AROUND OUTER PERIPHERAL SURFACE THEREOF AND ENDOSCOPE HAVING THE SAME

(71) Applicant: FUJIFILM Corporation, Tokyo (JP)

(72) Inventor: Yoshihiro Ueda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 482 days.

(21) Appl. No.: 17/170,814

(22) Filed: Feb. 8, 2021

(65) Prior Publication Data
US 2021/0219827 A1 Jul. 22, 2021

Related U.S. Application Data

(63) Continuation of application No. PCT/JP2019/035997, filed on Sep. 13, 2019.

(30) Foreign Application Priority Data

Sep. 20, 2018 (JP) .................. 2018-176266

(51) Int. Cl.
*A61B 1/00* (2006.01)
*A61B 1/005* (2006.01)
(Continued)

(52) U.S. Cl.
CPC ............ *A61B 1/0011* (2013.01); *A61B 1/005* (2013.01); *A61B 1/018* (2013.01); *A61B 1/015* (2013.01); *A61B 1/05* (2013.01)

(58) Field of Classification Search
CPC ..... A61B 1/0011; A61B 1/018; A61B 1/0055; A61M 25/0012
(Continued)

(56) References Cited

U.S. PATENT DOCUMENTS 4,236,509 A * 12/1980 Takahashi ............ A61B 1/0055
138/122
4,967,732 A * 11/1990 Inoue .................. A61B 1/00137
600/149
(Continued)

FOREIGN PATENT DOCUMENTS

| CN | 102548462 | 7/2012 |
| CN | 103957983 | 7/2014 |

(Continued)

OTHER PUBLICATIONS

Bladen PTFE, pp. 1-2 https://www.bladenptfe.com/difference-between-virgin-ptfe-eptfe-modified-ptfe-and-filled-ptfe/.*
(Continued)

*Primary Examiner* — John P Leubecker
*Assistant Examiner* — Li-Ting Song
(74) *Attorney, Agent, or Firm* — JCIPRNET

(57) ABSTRACT

Provided is an endoscope tube that has flexibility to withstand use in a flexible endoscope even in a case where the diameter is increased and easily detects damage to a fluororesin layer that forms an inner peripheral surface. The endoscope tube 100 includes an airtight inner layer tube member 101 that is made of a fluororesin, a permeable outer layer member 102 that has a hardness lower than that of the inner layer tube member 101 and covers an outer peripheral surface of the inner layer tube member 101, and a coil-shaped reinforcing member 103 that is wound around a spiral groove part 104 formed on an outer peripheral surface of the outer layer member 102. The endoscope 2 includes a treatment tool insertion channel 23 formed by the endoscope tube 100 in an insertion part 10.

7 Claims, 7 Drawing Sheets

(51) Int. Cl.
*A61B 1/015* (2006.01)
*A61B 1/018* (2006.01)
*A61B 1/05* (2006.01)

(58) Field of Classification Search
USPC ........................................................ 600/104
See application file for complete search history.

(56) References Cited

U.S. PATENT DOCUMENTS

| | | | |
|---|---|---|---|
| 6,464,632 B1* | 10/2002 | Taylor | A61B 1/005 138/174 |
| 6,977,105 B1* | 12/2005 | Fujieda | A61L 29/126 138/140 |
| 8,911,354 B2* | 12/2014 | Okada | A61B 1/00073 600/153 |
| 9,044,139 B2 | 6/2015 | Takahashi | |
| 10,022,518 B2 | 7/2018 | Yamashita et al. | |
| 2003/0181785 A1* | 9/2003 | Viebach | F15B 7/001 600/152 |
| 2005/0020882 A1 | 1/2005 | Hosoi et al. | |
| 2007/0255105 A1* | 11/2007 | Ochi | A61B 1/00071 600/153 |
| 2009/0112066 A1* | 4/2009 | Yago | A61B 1/00071 264/255 |
| 2011/0071541 A1* | 3/2011 | Prisco | A61B 34/37 606/130 |
| 2012/0180896 A1* | 7/2012 | Takahashi | A61B 1/0056 427/2.12 |
| 2019/0029503 A1 | 1/2019 | Hanai et al. | |
| 2020/0000312 A1* | 1/2020 | Nakaji | A61B 1/0057 |

FOREIGN PATENT DOCUMENTS

| | | |
|---|---|---|
| EP | 0605243 | 7/1994 |
| JP | H02118502 | 9/1990 |
| JP | H0591973 | 4/1993 |
| JP | 2000107122 | 4/2000 |
| JP | 2001046314 | 2/2001 |
| JP | 3184387 | 7/2001 |
| JP | 2001314368 | 11/2001 |
| JP | 2002187225 | 7/2002 |
| JP | 2002204778 | 7/2002 |
| JP | 2002315834 | 10/2002 |
| JP | 2005021243 | 1/2005 |
| JP | 2008054786 | 3/2008 |
| JP | 2008229067 | 10/2008 |
| JP | 2009018069 | 1/2009 |
| JP | 201214128 | 1/2012 |
| JP | 2013255577 | 12/2013 |
| WO | 2012077760 | 6/2012 |
| WO | WO-2012077760 A1 * | 6/2012 ........ A61B 1/0011 |
| WO | 2014123983 | 8/2014 |
| WO | 2017175709 | 10/2017 |

OTHER PUBLICATIONS

"Search Report of Europe Counterpart Application", issued on Oct. 13, 2021, pp. 1-7.
"International Search Report (Form PCT/ISA/210) of PCT/JP2019/035997," mailed on Dec. 3, 2019, with English translation thereof, pp. 1-5.
"Written Opinion of the International Searching Authority (Form PCT/ISA/237) of PCT/JP2019/035997," mailed on Dec. 3, 2019, with English translation thereof, pp. 1-9.
"Office Action of Japan Counterpart Application", issued on Jun. 7, 2022, with English translation thereof, p. 1-p. 5.
"Office Action of Japan Counterpart Application", issued on Jan. 11, 2022, with English translation thereof, p. 1-p. 4.
Office Action of Japan Counterpart Application, with English translation thereof, issued on Apr. 4, 2023, pp. 1-13.
"Office Action of Europe Counterpart Application", issued on Oct. 17, 2023, pp. 1-5.
Office Action of China Counterpart Application, with English translation thereof, issued on Feb. 1, 2024, pp. 1-16.

* cited by examiner

ENDOSCOPE TUBE WITH REINFORCING MEMBER WOUND AROUND OUTER PERIPHERAL SURFACE THEREOF AND ENDOSCOPE HAVING THE SAME

CROSS-REFERENCE TO RELATED APPLICATIONS

This application is a Continuation of PCT International Application No. PCT/JP2019/035997 filed on Sep. 13, 2019, which claims priority under 35 U.S.C § 119(a) to Japanese Patent Application No. 2018-176266 filed on Sep. 20, 2018. Each of the above application(s) is hereby expressly incorporated by reference, in its entirety, into the present application.

BACKGROUND OF THE INVENTION

1. Field of the Invention

The present invention relates to an endoscope tube and an endoscope.

2. Description of the Related Art

A plurality of tubes are built in an insertion part of a flexible endoscope, for example, a tube forming a treatment tool insertion channel is built in the insertion part. The flexible endoscope including the insertion part that is flexibly deformed in accordance with the shape of a human body lumen can reduce invasion to a subject, and the endoscope tube built in the insertion part is required to be flexible against bending. Also, the endoscope tube is required to maintain a constant cross-sectional shape against bending so as not to hinder the insertion of a treatment tool and the flow of a fluid. Moreover, since an inner peripheral surface of the tube forming the treatment tool insertion channel is in sliding contact with the treatment tool, it is preferable that the inner peripheral surface has low friction and high hardness. Additionally, since the flexible endoscope is cleaned, disinfected, and sterilized and repeatedly used, the endoscope tube is also required to have airtightness and chemical resistance. Fluororesin such as polytetrafluoroethylene (PTFE) is often used as a material for an endoscope tube that satisfies these conditions.

For example, an endoscope tube described in JP2002-204778A includes an inner layer made of a fluororesin and an outer layer made of a composite material of a fluororesin and a polyimide-based resin, a spiral groove is formed on the outer peripheral surface of an outer layer, and a metallic spiral material is wound around the spiral groove. The endoscope tube is reinforced with a metallic spiral material wound around the spiral groove, and the constant cross-sectional shape thereof is maintained against bending. Additionally, an endoscope tube described in JP2013-255577A also has a spiral groove formed on an outer peripheral surface of a tube body made of a fluororesin, and a coil member is wound around the spiral groove. Also, in the endoscope tube described in JP2013-255577A, the outer peripheral surface of the tube body around which the coil member is wound is covered with a polyurethane resin.

SUMMARY OF THE INVENTION

The number of treatments using the flexible endoscope is increasing year by year, and in the clinical practice of the flexible endoscope, countermeasures for treatment tools that realize more advanced treatments are required. In order to meet this demand, it is considered to increase the diameter of the treatment tool insertion channel so that various treatment tools can be inserted. However, as the diameter of the treatment tool insertion channel increases, the bending stiffness of the endoscope tube forming the treatment tool insertion channel increases. In a case where the bending stiffness of the endoscope tube is increased, the operability in a case where the insertion part is bent may degrade, and the life of a wire for driving a bending mechanism may be shortened.

In order to suppress an increase in the bending stiffness of the tube accompanying the increase in diameter, it is effective to reduce the thickness of a fluororesin layer having a relatively high hardness. However, in the endoscope tube described in JP2002-204778A, the spiral groove is formed on the outer peripheral surface of the outer layer containing the fluororesin, and the tube is reinforced by winding the metallic spiral material around the spiral groove. The same applies to the endoscope tube described in JP2013-255577A, the spiral groove is formed on the outer peripheral surface of the tube body made of the fluororesin, and the tube is reinforced by winding the coil member around the spiral groove. In order to form the spiral groove, a certain thickness or more is required for the outer layer or the tube body, which is an obstacle in suppressing the increase in the bending stiffness of the tube.

Additionally, the fluororesin layer typically forms the inner peripheral surface of the tube, and in a case where the thickness of the fluororesin layer is reduced, the durability against wear and perforation decreases. Also, in the endoscope tube described in JP2002-204778A, the inner layer, which is the fluororesin layer forming the inner peripheral surface, is covered with the outer layer made of the composite material of the fluororesin and the polyimide-based resin. In the endoscope tube described in JP2013-255577A, the tube body, which is the fluororesin layer forming the inner peripheral surface, is covered with the polyurethane resin. In these cases, even in a case where a hole is made in the fluororesin layer forming the inner peripheral surface, the airtightness of the entire tube is maintained, and there is a concern that it may be overlooked that the hole is made in the fluororesin layer.

The present invention has been made in view of the above-described circumstances, and an object thereof is to provide an endoscope tube that has flexibility to withstand use in a flexible endoscope even in a case where the diameter is increased and easily detects damage to a fluororesin layer that forms an inner peripheral surface.

An endoscope tube of an aspect of the present invention includes an airtight inner layer tube member that is made of a fluororesin; a permeable outer layer member that has a hardness lower than that of the inner layer tube member and covers an outer peripheral surface of the inner layer tube member; and a coil-shaped reinforcing member that is wound around a spiral groove part formed on an outer peripheral surface of the outer layer member.

Additionally, the endoscope according to the aspect of the present invention includes a treatment tool insertion channel formed by the endoscope tube in an insertion part.

According to the present invention, it is possible to provide an endoscope tube that has flexibility to withstand use in a flexible endoscope even in a case where the diameter is increased and easily detects damage to a fluororesin layer that forms an inner peripheral surface.

DESCRIPTION OF THE PREFERRED EMBODIMENTS

Figure 1:
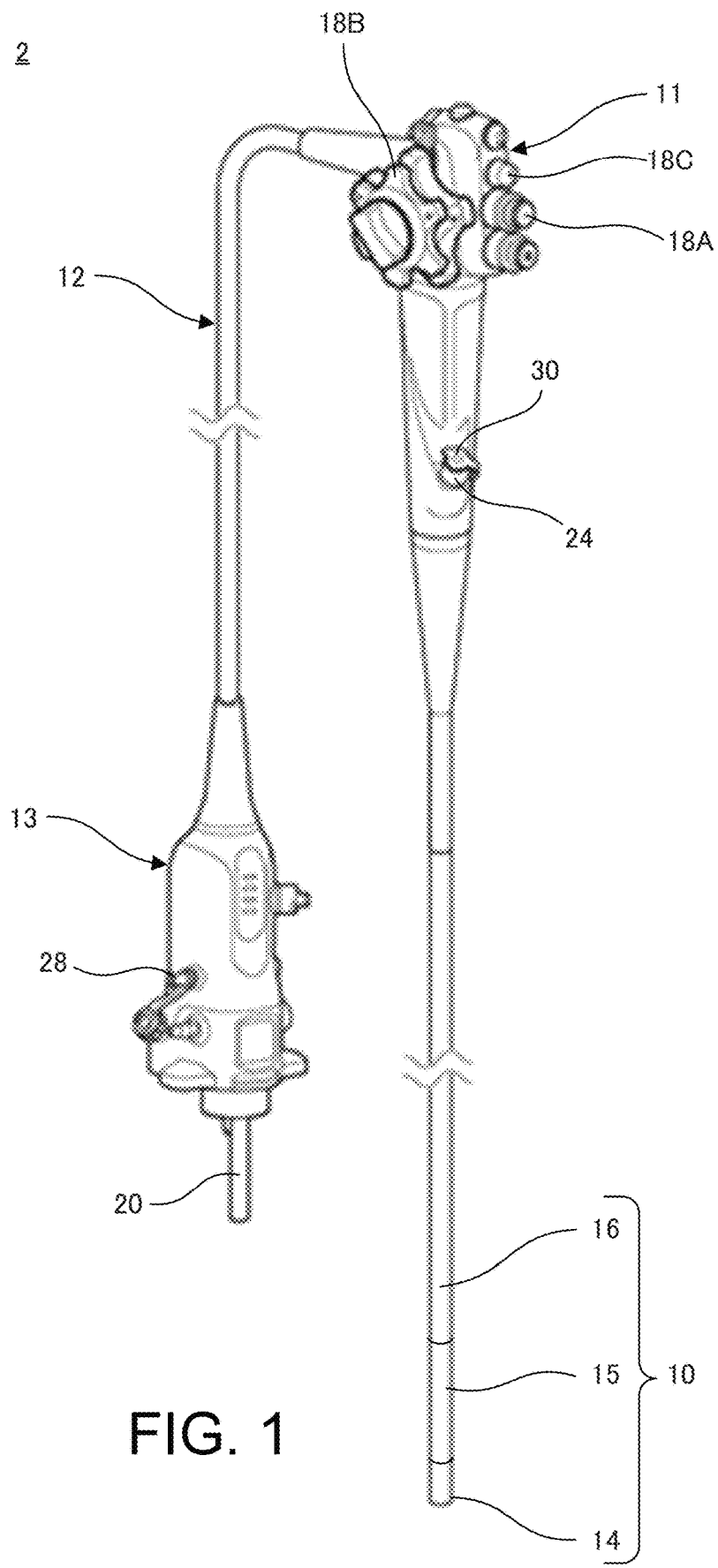
FIG. 1 is a perspective view of an example of an endoscope for explaining an embodiment of the present invention.
Figure 2:
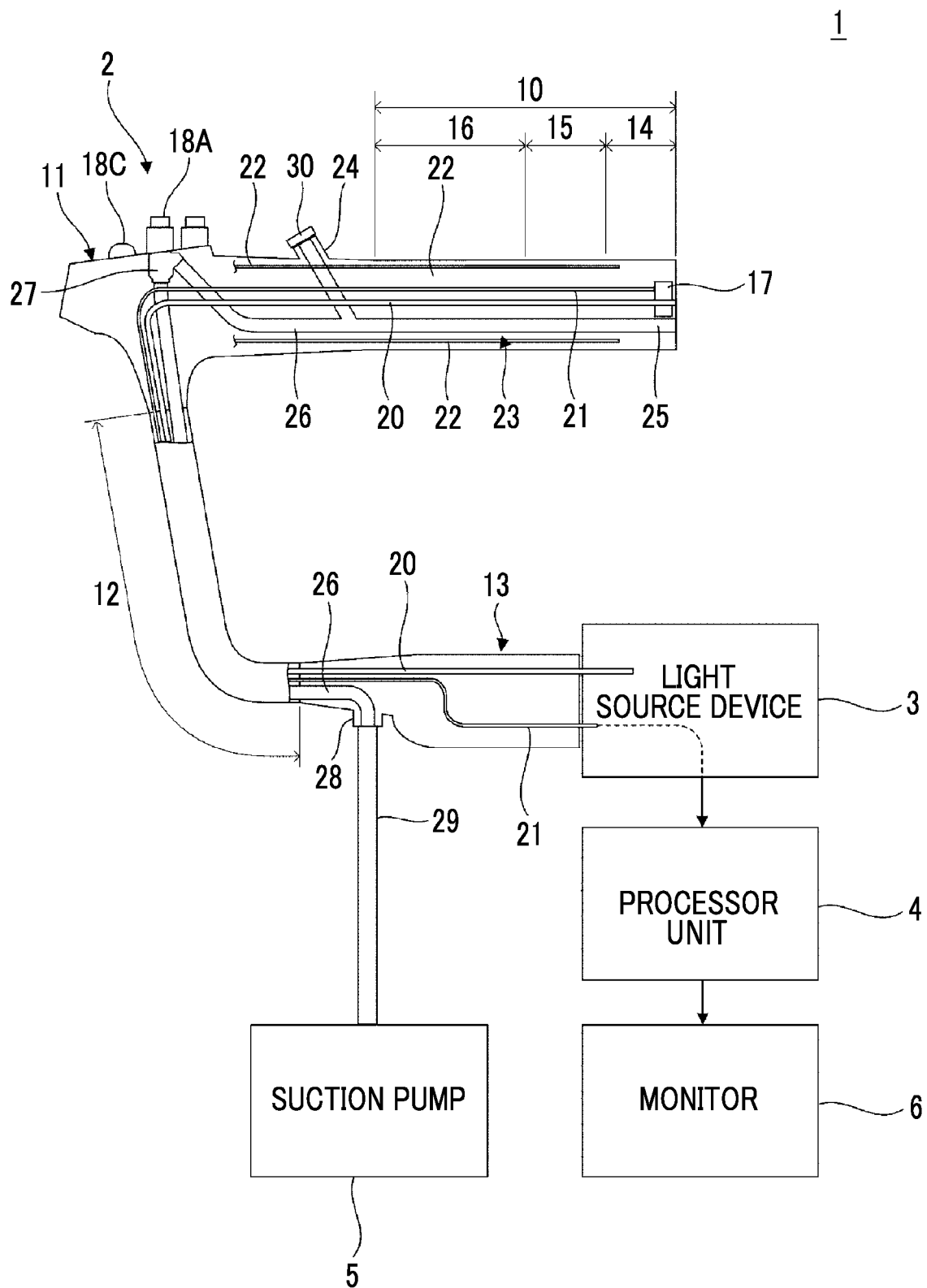
FIG. 2 is a schematic view of an example of an endoscope system including the endoscope of FIG. 1.

FIG. 1 illustrates an example of an endoscope for explaining an embodiment of the present invention, and FIG. 2 illustrates an example of an endoscope system including the endoscope of FIG. 1.

The endoscope system 1 comprises an endoscope 2, a light source device 3, a processor unit 4, and a suction pump 5. An endoscope 2 is a flexible endoscope and has an insertion part 10 to be inserted into a subject, an operating part 11 connected to the insertion part 10, and a universal cord 12 extending from the operating part 11, and a terminal of the universal cord 12 is provided with a connector 13 to be connected to the light source device 3.

The insertion part 10 is constituted of a distal end part 14, a bending part 15 connected to the distal end part 14, and a flexible part 16 that connects the bending part 15 and the operating part 11 to each other. An imaging unit 17 including imaging elements, such as a charge coupled device (CCD) image sensor and a complementary metal oxide semiconductor (CMOS) image sensor, is mounted on the distal end part 14. The bending part 15 is configured to be bendable, and bending of the bending part 15 is operated by the operating part 11. Additionally, the flexible part 16 is configured to be flexible so as to be deformable along the shape of an insertion path of the subject.

The operating part 11 is provided with an operation button 18A that operates suction using the suction pump 5, an operating knob 18B that operates the bending of the bending part 15, an operation button 18C that operates imaging using the imaging unit 17, and the like. Additionally, the operating part 11 is provided with an inlet portion 24 of the treatment tool insertion channel 23 into which a treatment tool is inserted.

A light guide 20 and an electrical cable 21 are provided inside the insertion part 10, the operating part 11, and the universal cord 12. The light guide 20 guides illumination light, which is to be generated by the light source device 3, to the distal end part 14. The electrical cable 21 transmits operating power, control signals, and captured image signals of the imaging unit 17 between the imaging unit 17 and the processor unit 4. The processor unit 4 generates captured image data from input captured image signals, and causes the generated captured image data to be displayed on the monitor 6 and recorded.

A plurality of operating wires 22 and a treatment tool insertion channel 23 are provided inside the insertion part 10 and the operating part 11. The operating wires 22 reach the distal end part 14 of the insertion part 10 from the operating part 11, and are pushed toward the distal end part 14 or pulled toward the operating part 11 in accordance with the operation of the operating knob 18B of the operating part 11. The bending part 15 of the insertion part 10 is bent in accordance with the push/pull of the operating wire 22. The treatment tool insertion channel 23 reaches the distal end part 14 of the insertion part 10 from the inlet portion 24 provided in the operating part 11, and an outlet portion 25 of the treatment tool insertion channel 23 opens to a distal end surface of the distal end part 14. A treatment tool inserted into the treatment tool insertion channel 23 through the opening of the inlet portion 24 is guided to the distal end part 14 of the insertion part 10 by the treatment tool insertion channel 23 and protrudes from the distal end part 14 through an opening of the outlet portion 25.

The treatment tool insertion channel 23 joins a suction tube 26 in the operating part 11. The suction tube 26 extends to the connector 13 via a valve 27 opened and closed by the operation button 18A and is connected to the suction pump 5 via the connection tube 29 connected to a mouthpiece 28 provided in the connector 13. By opening the valve 27, the fluid, such as blood, is suctioned from the opening of the outlet portion 25 of the treatment tool insertion channel 23 to the suction pump 5 through the suction tube 26. In addition, a forceps valve 30 having an on-off valve is mounted on the inlet portion 24, and as the opening of the inlet portion 24 is closed by the forceps valve 30 at the time of suction, the internal pressure of the treatment tool insertion channel 23 becomes negative pressure.

In addition, the endoscope 2 may have a channel other than the treatment tool insertion channel 23. An air and water supply channel, which sends a gas (for example, air) and a liquid (for example, water) used for cleaning an observation window of the imaging unit 17 to the distal end part 14, can be exemplified as another channel. The air and water supply channel is provided inside the insertion part 10, the operating part 11, and the universal cord 12 and is connected to a water supply tank (not illustrated) via the connector 13.

Figure 3:
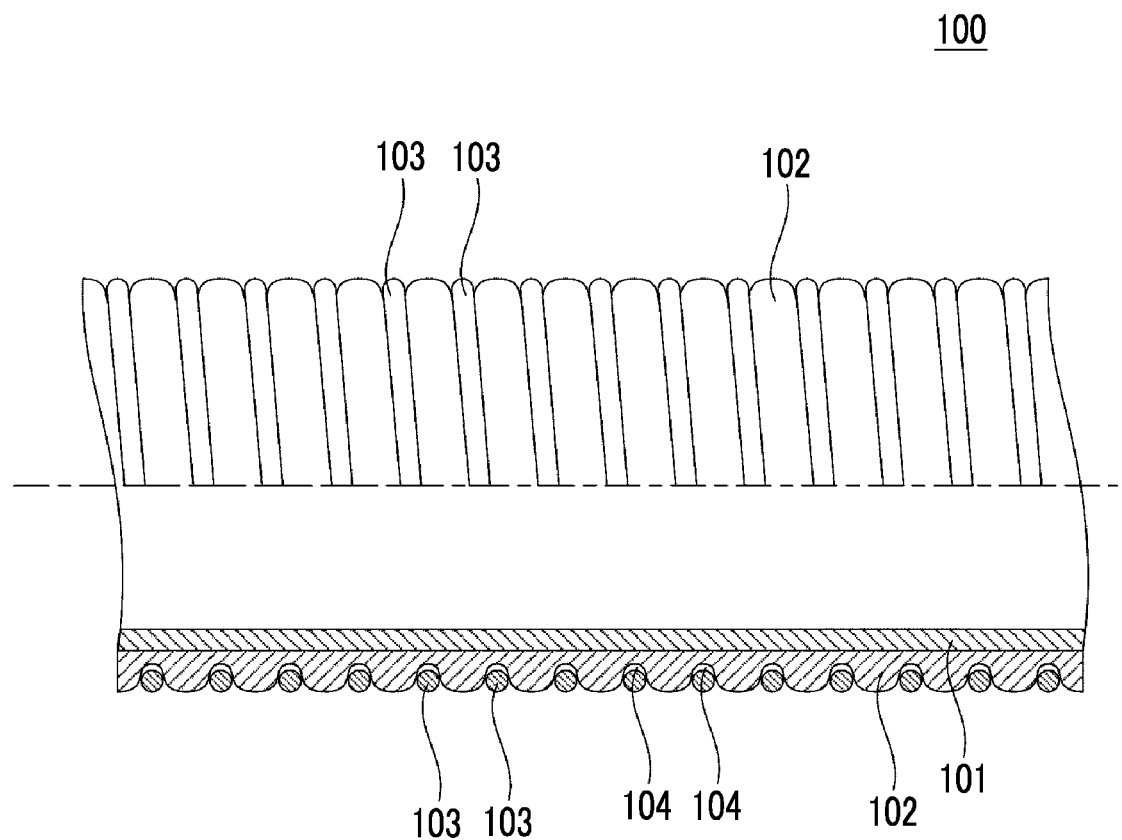
FIG. 3 is a partial cross-sectional view of an example of the endoscope tube for explaining the embodiment of the present invention.

FIG. 3 illustrates an example of the endoscope tube for explaining the embodiment of the present invention.

The endoscope tube 100 illustrated in FIG. 3 is used, for example, for the treatment tool insertion channel 23 of the endoscope 2 but may be used for channels (air and water supply channel and the like) other than the treatment tool insertion channel 23. The tube 100 includes an inner layer tube member 101, an outer layer member 102, and a coil-shaped reinforcing member 103.

The inner layer tube member 101 forms an inner peripheral surface of the tube 100, and in a case where the tube 100 is used for the treatment tool insertion channel 23, the inner layer tube member 101 is in sliding contact with a treatment tool inserted into the treatment tool insertion channel 23. The inner layer tube member 101 is made of a fluororesin having low friction and high hardness and is airtight. Fluororesin is, for example, non-foamed polytetrafluoroethylene (PTFE), perfluoroalkoxy alkane (PFA), or perfluoroethylene propene copolymer (FEP).

The outer layer member 102 is formed in a tubular shape and covers the entire outer periphery of the inner layer tube member 101. A spiral groove part 104 is formed on an outer peripheral surface of the outer layer member 102. Additionally, the outer layer member 102 has permeability, and the hardness of the outer layer member 102 is smaller than the hardness of the inner layer tube member 101. In addition, the hardness of the inner layer tube member 101 and the outer layer member 102 is the hardness obtained by a micro Vickers hardness test or a hardness test using a nanoindentation method. The material of the outer layer member 102 is, for example, a porous fluororesin such as the foamed PTFE.

The outer layer member 102 can be formed by, for example, extrusion molding. Specifically, the material of the outer layer member 102 that has been heated and melted is extruded from a mold, and the inner layer tube member 101 that is moved through the mold is continuously covered with the material extruded from the mold. Then, the outer layer member 102 is formed by solidifying the material covering the inner layer tube member 101. Another method for forming the outer layer member 102 is a method in which only the outer layer member 102 is formed in advance, then the inner layer tube member 101 is covered with the outer layer member 102, and the outer layer member 102 is joined by heating while clamping. The spiral groove part 104 can be formed by, for example, laser machining, pressing of a metal wire in a heated state, or the like.

The coil-shaped reinforcing member 103 is formed, for example, by forming a metal wire such as a stainless steel wire into a coil shape, and is strong against deformation of a cross-sectional shape such as being crushed flat and flexible against bending. The coil-shaped reinforcing member 103 is wound around the spiral groove part 104 of the outer layer member 102. In a cross-section perpendicular to a central axis of the wire forming the coil-shaped reinforcing member 103, the entire coil-shaped reinforcing member 103 may be housed in the spiral groove part 104, or a portion of the coil-shaped reinforcing member 103 may protrude out of the spiral groove part 104.

In a case where the tube 100 is compared with a tube having the same internal diameter and external diameter as the tube 100 and having the same entire thickness as the inner layer tube member 101 made of fluororesin, the tube 100 including the outer layer member 102 having a lower hardness than that of the inner layer tube member 101 has a relatively small bending stiffness, which is advantageous for increasing the diameter.

Additionally, in a case where the tube 100 is bent and the bent portions of the inner layer tube member 101 and the outer layer member 102 are broken, the cross-sectional shapes of the inner layer tube member 101 and the outer layer member 102 are flatly crushed. However, such crushing is limited by the coil-shaped reinforcing member 103 wound around the outer peripheral surface of the outer layer member 102. Also, the coil-shaped reinforcing member 103 is wound around the spiral groove part 104 of the outer layer member 102, and the relative movement between the coil-shaped reinforcing member 103 and the outer layer member 102 in the axial direction is restricted. Therefore, even in a case where the tube 100 is bent, the coil-shaped reinforcing member 103 is held by the bent portions of the inner layer tube member 101 and the outer layer member 102. Accordingly, the cross-sectional shapes of the inner layer tube member 101 and the outer layer member 102 are kept constant against the bending of the tube 100, and the insertion of the treatment tool and the flow of the fluid are guaranteed.

In addition, the smaller the thickness of each of the inner layer tube member 101 and the outer layer member 102, the smaller the bending stiffness of the tube 100. However, the thickness sufficient to allow the inner layer tube member 101 and the outer layer member 102 to integrally self-hold the cross-sectional shape is necessary, and the thickness thereof is appropriately set depending on, for example, the diameter of the tube 100. Additionally, as earlier described, since the fluororesin having a relatively high hardness is used for the inner layer tube member 101, the inner layer tube member 101 has a small wall thickness in order to suppress the bending stiffness and is broken even with a relatively large bending radius. Thus, it is desirable that the outer layer member 102 has a low hardness and is thicker than the inner layer tube member 101 in order to prevent the breaking of the inner layer tube member 101. Based on the above, in the thickness sufficient to allow the inner layer tube member 101 and the outer layer member 102 to integrally self-hold the cross-sectional shape, from the viewpoint of reducing the bending stiffness of the tube 100, the thickness of the outer layer member 102 is preferably larger than half the thickness of the inner layer tube member 101, the thickness of the outer layer member 102 is more preferably larger than the thickness of the inner layer tube member 101, and a value H1/H2 of the ratio of a hardness H1 of the inner layer tube member 101 to a hardness H2 of the outer layer member 102 is larger than a value T2/T1 of the ratio of a thickness T2 of the outer layer member 102 to a thickness T1 of the inner layer tube member 101. The hardness referred to here is, for example, a hardness obtained by a hardness test performed by a micro Vickers hardness tester or a nanoindentation method. It is desirable that the hardness H1 of the inner layer tube member 101 and the hardness H2 of the outer layer member 102 obtained by these measurement methods and a wall thickness T1 of the inner layer tube member 101 and a wall thickness T2 of the outer layer member 102 have the following relationships. For example, in a case where the wall thickness of the inner layer tube member 101 is 0.1 mm and the wall thickness of the outer layer member 102 is 0.4 mm, T2/T1 is 4. In this case, in a case where the hardness H1 of the inner layer tube member 101 is 80 MPa, the hardness H2 of the outer layer member 102 is desirably less than 20 MPa, and thereby, H1/H2 is larger than T2/T1.

Additionally, the bending stiffness of the tube 100 is affected by the cross-sectional secondary moment of the tube 100, and particularly, the cross-sectional secondary moment of the inner layer tube member 101 having a relatively high hardness. In a case where the thickness of the inner layer tube member 101 is constant in the circumferential direction, the internal diameter of the inner layer tube member 101 is d [mm], and the external diameter is D [mm], the cross-sectional secondary moment of the inner layer tube member 101 is $\pi/64 \times (D^4 - d^4)$, preferably $30 < D^4 - d^4 < 180$. Here, mm represents millimeters.

Figure 4:
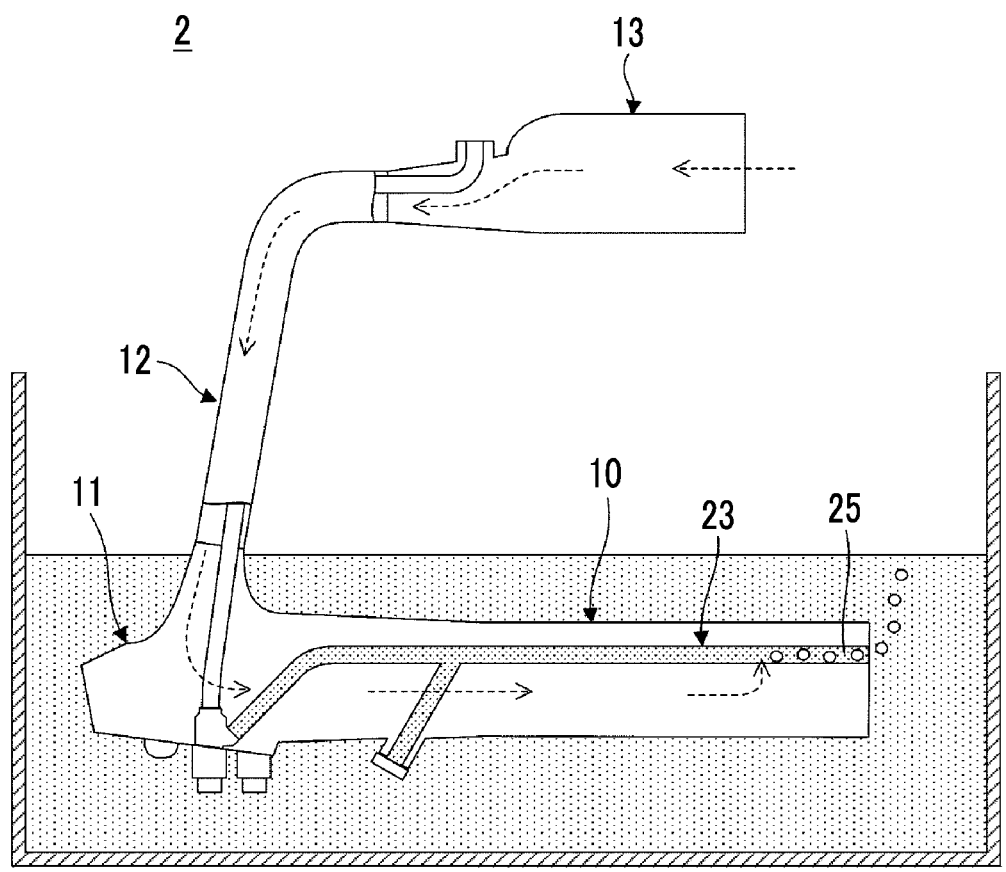
FIG. 4 is a schematic view of an inspection method for inspecting damage to an inner layer tube member of FIG. 3.
Figure 5:
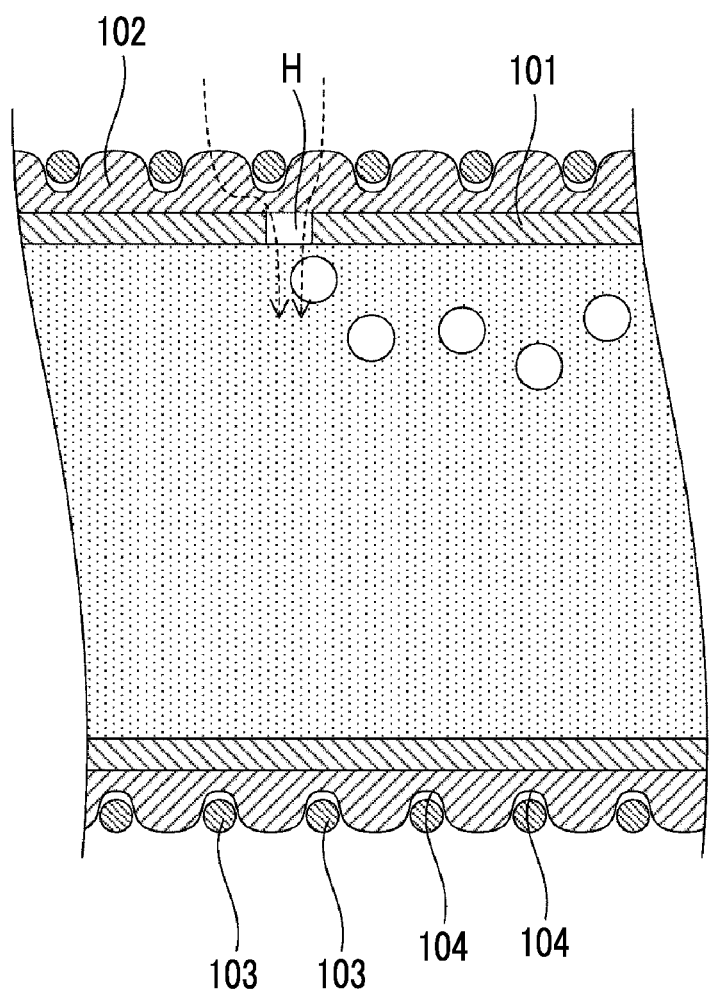
FIG. 5 is an enlarged cross-sectional view illustrating a damaged spot of the inner layer tube member of FIG. 3.

FIGS. 4 and 5 illustrate an example of an inspection method for inspecting the presence or absence of damage to the inner layer tube member 101. In addition, it is assumed that the tube 100 is used for the treatment tool insertion channel 23 of the endoscope 2.

As illustrated in FIG. 4, a gas such as air is supplied to the inside of the insertion part 10 and the outside of the treatment tool insertion channel 23 in a state where the endoscope 2 is submerged in the liquid. The gas is introduced from the connector 13, for example, as illustrated by a broken line arrow in FIG. 4, and is supplied to the inside of the insertion part 10 and the outside of the treatment tool insertion channel 23 through the inside of the universal cord 12 and the operating part 11.

In a case where the inner layer tube member 101 is damaged and the airtightness of the inner layer tube member 101 is lost, the gas supplied to the inside of the insertion part 10 and the outside of the treatment tool insertion channel 23 leaks to the inside of the treatment tool insertion channel 23 through the damaged spot of the inner layer tube member 101 in response to an increase in the pressure of the gas. Then, the gas, which has leaked to the inside of the treatment tool insertion channel 23, is released into the liquid as bubbles from the opening of the outlet portion 25 of the treatment tool insertion channel 23, for example. Accordingly, damage to the inner layer tube member 101 is detected.

FIG. 5 illustrates a damaged spot of the inner layer tube member 101 in an enlarged manner, and a hole H is open to the inner layer tube member 101. Although the hole H is covered with the outer layer member 102, the outer layer member 102 has permeability, and the outer peripheral surface of the outer layer member 102 is exposed except for the spiral groove part 104 around which the coil-shaped reinforcing member 103 is wound. The gas supplied to the inside of the insertion part 10 and the outside of the treatment tool insertion channel 23 flows into the hole H from the exposed outer peripheral surface of the outer layer member 102 and leaks to the inside of the treatment tool insertion channel 23 through the hole H.

Meanwhile, in a case where the outer layer member 102 is made of a polyimide resin similar to the endoscope tube described in JP2002-204778A and in a case where the outer peripheral surface of the outer layer member 102 around which the coil-shaped reinforcing member 103 is wound similar to the endoscope tube described in JP2013-255577A is covered with the polyurethane resin, the outermost outer peripheral surface of the tube 100 becomes airtight, and even in a case where the inner layer tube member 101 has the hole H, the airtightness of the entire tube 100 is maintained. As a result, the gas supplied to the inside of the insertion part 10 and the outside of the treatment tool insertion channel 23 does not leak to the inside of the treatment tool insertion channel 23, and the presence of the hole H is overlooked.

Figure 6:
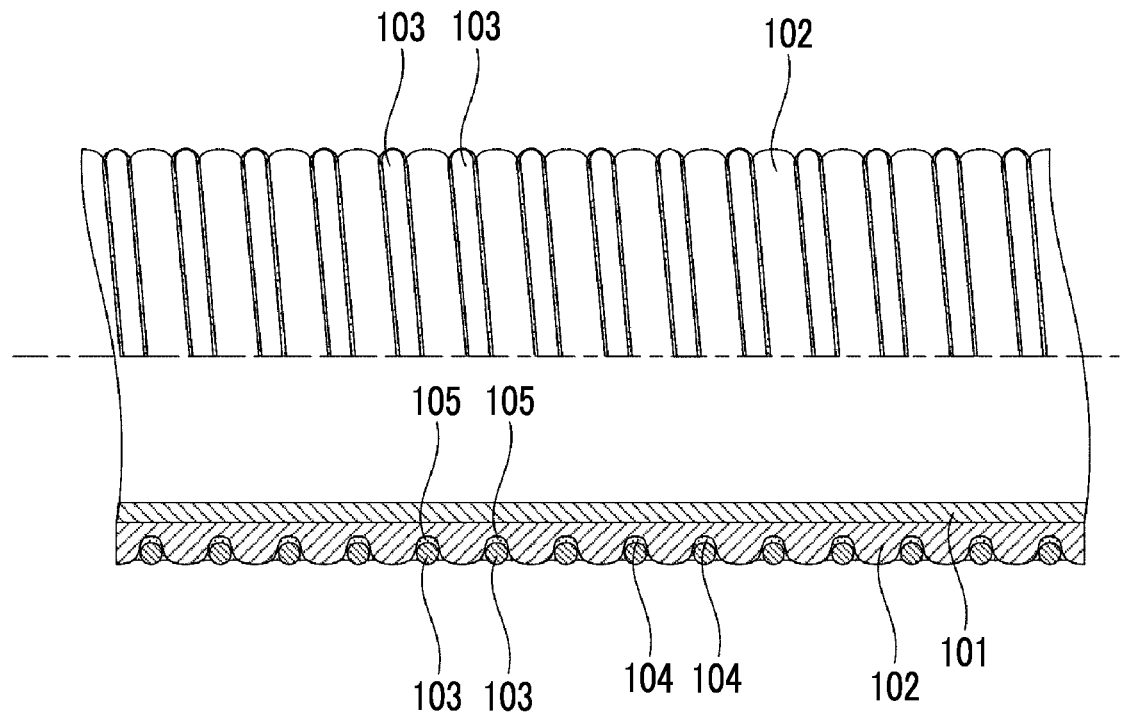
FIG. 6 is a partial cross-sectional view of a modification example of the endoscope tube of FIG. 3.

FIG. 6 illustrates a modification example of the tube 100.

In the example illustrated in FIG. 6, the coil-shaped reinforcing member 103 and the spiral groove part 104 are bonded to each other with an adhesive 105 filled only in the spiral groove part 104. According to the present example, in a case where the tube 100 is bent, the coil-shaped reinforcing member 103 is reliably held by the bent portions of the inner layer tube member 101 and the outer layer member 102. Accordingly, the cross-sectional shapes of the inner layer tube member 101 and the outer layer member 102 are kept constant against the bending of the tube 100, and the insertion of the treatment tool and the flow of the fluid are guaranteed.

Also, the adhesive 105 is filled only in the spiral groove part 104, and the outer peripheral surface of the outer layer member 102 is exposed except for the spiral groove part 104. Therefore, even in a case where the adhesive 105 is airtight, damage to the inner layer tube member 101 can be detected by the inspection method illustrated in FIGS. 4 and 5.

The adhesive 105 filled only in the spiral groove part 104 may be made of a thermoplastic resin pre-coated on the surface of the coil-shaped reinforcing member 103. In this case, the coil-shaped reinforcing member 103 is heated in a state where the coil-shaped reinforcing member 103 is wound around the spiral groove part 104, and the thermoplastic resin pre-coated on the surface of the coil-shaped reinforcing member 103 is first melted. Then, as the melted thermoplastic resin is re-solidified inside the spiral groove part 104, the thermoplastic resin is filled only in the spiral groove part 104. The thermoplastic resin filled in the spiral groove part 104 becomes the adhesive 105, and the coil-shaped reinforcing member 103 and the spiral groove part 104 are bonded to each other. Of course, the adhesive 105 may be coated on the spiral groove part 104.

Figure 7:
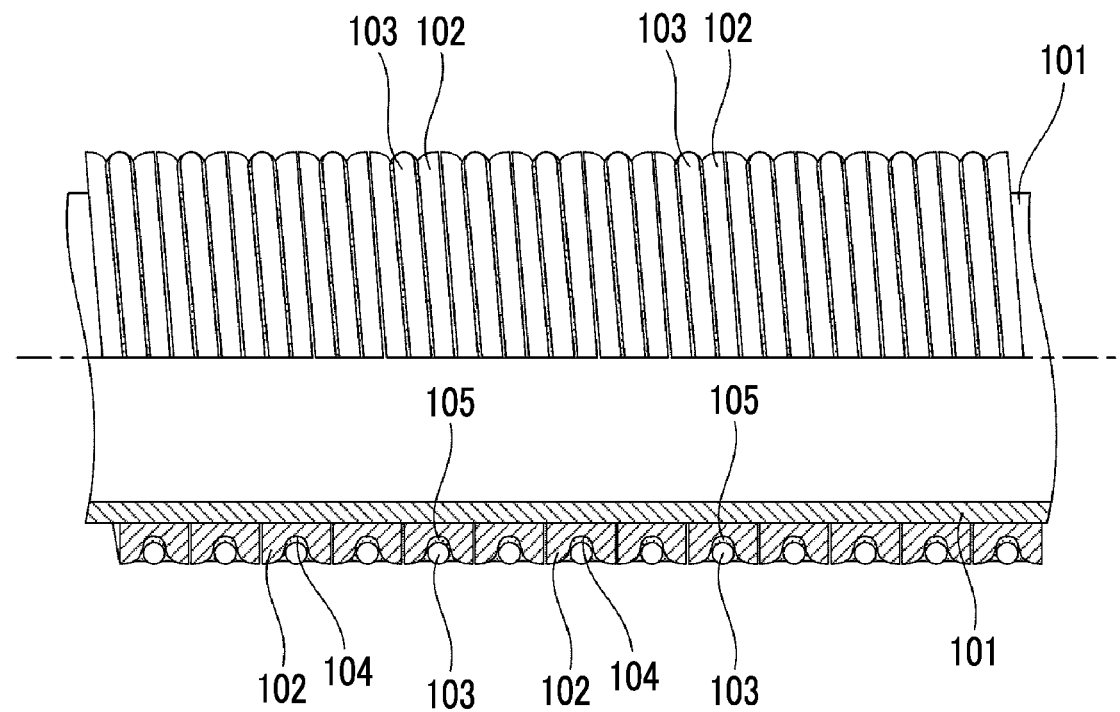
FIG. 7 is a partial cross-sectional view of another modification example of the endoscope tube of FIG. 3.

FIG. 7 illustrates another modification example of the tube 100.

In the example illustrated in FIG. 7, the outer layer member 102 is formed in a belt shape and is spirally wound around the outer peripheral surface of the inner layer tube member 101. The belt-shaped outer layer member 102 spirally wound around the outer peripheral surface of the inner layer tube member 101 is flexible against bending similar to the coil-shaped reinforcing member 103. According to the present example, the bending stiffness of the tube 100 can be further reduced. Additionally, since the outer peripheral surface of the outer layer member 102 is exposed, damage to the inner layer tube member 101 can be detected by the inspection method illustrated in FIGS. 4 and 5.

According to the tube 100 and its modification example described above, the bending stiffness can be reduced, which is advantageous for increasing the diameter. The internal diameter of the treatment tool insertion channel 23 is generally 4 mm or less. However, by using the tube 100, a large-diameter treatment tool insertion channel 23 having flexibility to withstand use in a flexible endoscope and having an internal diameter of 5 mm or more and 8 mm or less can be realized.

Figure 8:
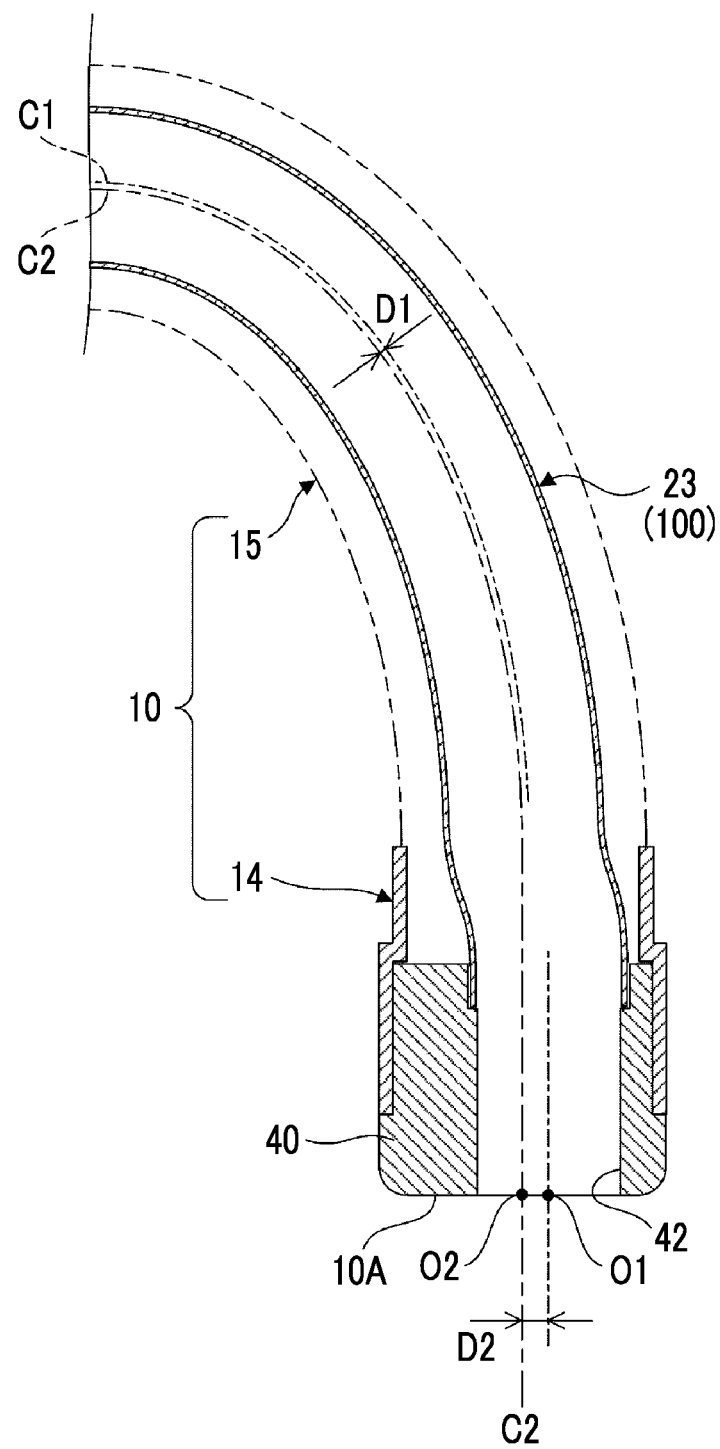
FIG. 8 is a schematic view of an endoscope in which an insertion part includes a treatment tool insertion channel formed by the endoscope tube of FIG. 3.

FIG. 8 illustrates an example of the disposition of the large-diameter treatment tool insertion channel 23 in the insertion part 10.

The treatment tool insertion channel 23 is formed by the tube 100 described above, and the internal diameter of the treatment tool insertion channel 23 is 5 mm or more and 8 mm or less. The external diameter of the insertion part 10 provided with such a large-diameter treatment tool insertion channel 23 is, for example, about 13 mm.

A distance D1 between a central axis C1 of the treatment tool insertion channel 23 in the bending part 15 of the insertion part 10 and a central axis C2 of the insertion part 10 is smaller than a distance D2 between a center O1 of an opening of the treatment tool insertion channel 23 in a distal end surface 10A of the insertion part 10 and a center O2 of the distal end surface 10A. In other words, the treatment tool insertion channel 23 is disposed on the central axis C2 of the insertion part 10 in the bending part 15 and is disposed off the central axis C2 of the insertion part 10 in the distal end part 14.

In the bending part 15, other built-in objects such as the light guide 20 (refer to FIG. 2), the electrical cable 21 (refer to FIG. 2), the plurality of operating wires 22 (refer to FIG. 2), and the air and water supply channel are disposed along the outer periphery of the treatment tool insertion channel 23 and in an appropriately dispersed manner in the circumferential direction, and the treatment tool insertion channel 23 is surrounded by these other built-in object. Accordingly, the treatment tool insertion channel 23 is held on the central axis C2 of the insertion part 10 in the bending part 15.

Meanwhile, the distal end part 14 has a columnar distal rigid part 40 that holds a built-in object such as the imaging unit 17 (refer to FIG. 2) mounted on the distal end part 14, and a through-hole 42 having a circular cross-sectional shape is formed in the distal rigid part 40 so as to penetrate the distal rigid part 40 in the axial direction. The tube 100, which forms the treatment tool insertion channel 23, is joined to the distal rigid part 40 so as to communicate with the through-hole 42. The through-hole 42 forms an opening of the treatment tool insertion channel 23 on the distal end surface 10A.

A central axis of the through-hole 42 deviates from a central axis of the distal rigid part 40 that coincides with the central axis C2 of the insertion part 10, and the tube 100 joined to the distal rigid part 40 so as to communicate with the through-hole 42 is appropriately flexed between the distal rigid part 40 and the bending part 15. Accordingly, the treatment tool insertion channel 23 is held off the central axis C2 of the insertion part 10 in the distal end part 14.

The bending part 15 is a part of the insertion part 10 that is repeatedly bent with the smallest radius of curvature. Since the treatment tool insertion channel 23 is held on the central axis C2 of the insertion part 10 in the bending part 15, the bending angle of the treatment tool insertion channel 23 can be equally small regardless of the bending direction of the bending part 15. Additionally, it is possible to suppress the axial displacement of the treatment tool insertion channel 23 accompanying bending and bending-back. Accordingly, the operability in a case where the bending part 15 is bent can be enhanced.

Manufacture examples of the endoscope tube will be described below.

A tube of Manufacture Example 1 has the same configuration as the tube 100 illustrated in FIG. 3, and the entire outer periphery of the airtight inner layer tube member 101 made of the fluororesin is covered with the permeable outer layer member 102 having a lower hardness than that of the inner layer tube member 101, and the coil-shaped reinforcing member 103 is wound around the spiral groove part 104 formed on the outer peripheral surface of the outer layer member 102. Tubes of Manufacture Example 2 and Manufacture Example 3 have the same configuration as the modification example of the tube 100 illustrated in FIG. 4, and the coil-shaped reinforcing member 103 and the spiral groove part 104 are bonded to each other with the adhesive 105 filled only in the spiral groove part 104. A tube of Manufacture Example 4 has the same configuration as the tube 100 illustrated in FIG. 3 except that the outer layer member 102 is made of urethane resin and is airtight. Additionally, a tube of Manufacture Example 5 has the same configuration as the tube 100 illustrated in FIG. 3 except that the coil-shaped reinforcing member 103 is omitted.

The internal diameter d and the external diameter D of the inner layer tube members 101 of the respective manufacture examples are as shown in Table 1. Table 1 shows the evaluation results of the bending stiffness and break resistance for the tubes of the respective manufacture examples and whether or not damage to the inner layer tube member 101 can be detected altogether. In addition, the bending stiffness was evaluated depending on a reaction force measured in a three-point bending test, and in a case where the fulcrum distance was 60 mm and the deflection amount was 3 mm, the bending stiffness in a tube having a reaction force of 5 N or less was evaluated as A, and the bending stiffness in a tube having a reaction force exceeding 5 N was evaluated as B. The break resistance was evaluated depending on whether or not a tube was broken in a case where the tube was bent with a radius of curvature of 20 mm, the break resistance was evaluated as A in a tube in which break did not occur, and the break resistance was evaluated as B in a tube in which break occurred. Additionally, the damage to the inner layer tube member 101 was detected by the inspection method illustrated in FIGS. 4 and 5.

TABLE 1

| | Inner Layer Tube Member | | | | Material | Coil- | | | |
| --- | --- | --- | --- | --- | --- | --- | --- | --- | --- |
| | Material | Internal Diameter d [mm] | External Diameter D [mm] | $D^4-d^4$ | of Outer Layer Member | shaped Reinforcing Member | Bending Resistance | Break Resistance | Damage Detection |
| Manufacture Example 1 | Fluororesin | 5 | 5.2 | 106 | Foamed PTFE | Yes | A | A | Possible |
| Manufacture Example 2 | Fluororesin | 6 | 6.1 | 89 | Foamed PTFE | Yes | A | A | Possible |
| Manufacture Example 3 | Fluororesin | 8 | 8.06 | 124 | Foamed PTFE | Yes | A | A | Possible |
| Manufacture Example 4 | Fluororesin | 6 | 6.6 | 602 | Urethane resin | Yes | B | A | Impossible |
| Manufacture Example 5 | Fluororesin | 6 | 6.1 | 89 | Foamed PTFE | No | A | B | Possible |

As shown in Table 1, in a case where the tubes of Manufacture Examples 1 to 3 were large-diameter tubes having an internal diameter d of 5 mm or more and 8 mm or less, both the bending stiffness and the break resistance was evaluated as A, and damage to the inner layer tube member 101 could also be detected. In contrast, in the tube of Manufacture Example 4 in which the outer layer member 102 was made of urethane resin, damage to the inner layer tube member 101 could not be detected. Additionally, in the tube of Manufacture Example 5 in which the coil-shaped reinforcing member 103 was omitted, the break resistance was evaluated as B.

Comparing Manufacture Example 2 and Manufacture Example 5 in which the internal diameter and external diameters of the inner layer tube member 101 are the same, it can be seen that the coil-shaped reinforcing member 103 can suppress the break of a tube with respect to bending without increasing the bending stiffness. Additionally, paying attention to the value of $D^4-d^4$ related to the cross-sectional secondary moment of the inner layer tube member 101, Manufacture Example 1 to Manufacture Example 3 all satisfy $30<D^4-d^4<180$. However, in Manufacture Example 4, the bending stiffness is evaluated as B, and the value of $D^4-d^4$ is 602. It can be seen from this result that $30<D^4-d^4<180$ is preferable.

As described above, an endoscope tube disclosed in the present specification includes an airtight inner layer tube member that is made of a fluororesin; a permeable outer layer member that has a hardness lower than that of the inner layer tube member and covers an outer peripheral surface of the inner layer tube member; and a coil-shaped reinforcing member that is wound around a spiral groove part formed on an outer peripheral surface of the outer layer member.

Additionally, in the endoscope tube disclosed in the present specification, the outer layer member is formed in a belt shape and is spirally wound around the outer peripheral surface of the inner layer tube member.

Additionally, in the endoscope tube disclosed in the present specification, the coil-shaped reinforcing member and the spiral groove part are bonded to each other with an adhesive filled only in the spiral groove part.

Additionally, in the endoscope tube disclosed in the present specification, the adhesive is obtained by melting and re-solidifying a thermoplastic resin pre-coated on a surface of the coil-shaped reinforcing member.

Additionally, in the endoscope tube disclosed in the present specification, a thickness of the outer layer member is larger than half a thickness of the inner layer tube member.

Additionally, in the endoscope tube disclosed in the present specification, a thickness of the outer layer member is larger than a thickness of the inner layer tube member, and a value of a ratio of a hardness of the inner layer tube member to a hardness of the outer layer member is larger than a value of a ratio of the thickness of the outer layer member to the thickness of the inner layer tube member.

Additionally, in the endoscope tube disclosed in the present specification, $30 < D^4 - d^4 < 180$ is established in a case where an internal diameter of the inner layer tube member is d millimeters and an external diameter of the inner layer tube member is D millimeters.

Additionally, in the endoscope tube disclosed in the present specification, the outer layer member contains a porous fluororesin.

Additionally, an endoscope disclosed in the present specification includes a treatment tool insertion channel formed in an insertion part by the endoscope tube.

Additionally, in the endoscope disclosed in the present specification, an internal diameter of the treatment tool insertion channel is 5 millimeters or more and 8 millimeters or less.

Additionally, in the endoscope disclosed in the present specification, wherein a distance between a central axis of the treatment tool insertion channel in the bending part of the insertion part and a central axis of the insertion part is smaller than a distance between a center of an opening of the treatment tool insertion channel on a distal end surface of the insertion part and a center of the distal end surface.

EXPLANATION OF REFERENCES

1: endoscope system
2: endoscope
3: light source device
4: processor unit
5: suction pump
6: monitor
10: insertion part
10A: distal end surface of insertion part
11: operating part
12: universal cord
13: connector
14: distal end part
15: bending part
16: flexible part
17: imaging unit
18A, 18C: operation button
18B: operating knob
20: light guide
21: electrical cable
22: operating wire
23: treatment tool insertion channel
24: inlet portion
25: outlet portion
26: suction tube
27: valve
28: mouthpiece
29: connection tube
30: forceps valve
40: distal rigid part
42: through-hole
100: endoscope tube
101: inner layer tube member
102: outer layer member
103: coil-shaped reinforcing member
104: spiral groove part
105: adhesive
C1: central axis of treatment tool insertion channel
C2: central axis of insertion part
D1, D2: distance
H: hole made in inner layer tube member
O1: center of opening of treatment tool insertion channel
O2: center of distal end surface of insertion part

What is claimed is:

1. An endoscope tube used for endoscopes, comprising:
   an airtight inner layer tube member made of a fluororesin;
   a permeable outer layer member that has a hardness lower than that of the inner layer tube member and covers an outer peripheral surface of the inner layer tube member, wherein the outer layer member contains a porous fluororesin; and
   a coil-shaped reinforcing member that is wound around a spiral groove part formed on an outer peripheral surface of the outer layer member,
   wherein the spiral groove part and the coil-shaped reinforcing member are bonded to each other with an adhesive filled only in a part of the spiral groove part,
   wherein a thickness of the outer layer member is larger than a thickness of the inner layer tube member, and
   a value of a ratio of a hardness of the inner layer tube member to a hardness of the outer layer member is larger than a value of a ratio of the thickness of the outer layer member to the thickness of the inner layer tube member,
   wherein $30 < D^4 - d^4 < 180$ is established in a case where an internal diameter of the inner layer tube member is d millimeters and an external diameter of the inner layer tube member is D millimeters.

2. The endoscope tube according to claim 1, wherein the outer layer member is formed in a belt shape and is spirally wound around the outer peripheral surface of the inner layer tube member.

3. The endoscope tube according to claim 2, wherein the adhesive is obtained by melting and re-solidifying a thermoplastic resin pre-coated on a surface of the coil-shaped reinforcing member.

4. The endoscope tube according to claim 1, wherein the adhesive is obtained by melting and re-solidifying a thermoplastic resin pre-coated on a surface of the coil-shaped reinforcing member.

5. An endoscope comprising:
   a treatment tool insertion channel formed in an insertion part by the endoscope tube according to claim 1.

6. The endoscope according to claim 5,
wherein an internal diameter of the treatment tool insertion channel is 5 millimeters or more and 8 millimeters or less.

7. The endoscope according to claim 6,
wherein a distance between a central axis of the treatment tool insertion channel in a bending part of the insertion part and a central axis of the insertion part is smaller than a distance between a center of an opening of the treatment tool insertion channel on a distal end surface of the insertion part and a center of the distal end surface.

* * * * *